(12) United States Patent
Fujiwara et al.

(10) Patent No.: US 11,538,552 B2
(45) Date of Patent: Dec. 27, 2022

(54) SYSTEM AND METHOD FOR CONTRASTIVE NETWORK ANALYSIS AND VISUALIZATION

(71) Applicant: FUJIFILM Business Innovation Corp., Tokyo (JP)

(72) Inventors: Takanori Fujiwara, Davis, CA (US); Jian Zhao, Waterloo (CA); Francine Chen, Menlo Park, CA (US)

(73) Assignee: FUJIFILM Business Innovation Corp., Tokyo (JP)

( * ) Notice: Subject to any disclaimer, the term of this patent is extended or adjusted under 35 U.S.C. 154(b) by 501 days.

(21) Appl. No.: 16/773,899

(22) Filed: Jan. 27, 2020

(65) Prior Publication Data
US 2021/0233607 A1 Jul. 29, 2021

(51) Int. Cl.
*G16B 15/00* (2019.01)
*G16B 20/00* (2019.01)
*G06N 20/00* (2019.01)
*G16B 5/00* (2019.01)
*G16H 50/70* (2018.01)
*G16B 40/00* (2019.01)

(52) U.S. Cl.
CPC ............ *G16B 15/00* (2019.02); *G06N 20/00* (2019.01); *G16B 5/00* (2019.02); *G16B 20/00* (2019.02); *G16B 40/00* (2019.02); *G16H 50/70* (2018.01)

(58) Field of Classification Search
CPC .......... G16B 15/00; G16B 5/00; G16B 20/00; G16B 40/00; G06N 20/00; G06N 3/0454; G06N 5/022; G06N 5/045; G16H 50/70; G16H 50/20; G06F 9/451; G06F 17/16
See application file for complete search history.

(56) References Cited

U.S. PATENT DOCUMENTS 8,943,106 B2 * 1/2015 Labbi .................... G06F 16/904
707/805
11,216,722 B2 * 1/2022 Nurvitadhi ............. G06N 3/063

OTHER PUBLICATIONS

Kato, G., et al., Threatening Event, National identity and Network Dynamics of Motivated Information Communication: Exploring Japanese Twitter during the Rise of Territorial Disputes, Apr. through Oct. 2012, Aug. 11, 2017, 113th American Political Science Association Annual Meeting, San Francisco, CA, 60 pgs.

(Continued)

*Primary Examiner* — Maroun P Kanaan
(74) *Attorney, Agent, or Firm* — Procopio, Cory, Hargreaves & Savitch LLP

(57) ABSTRACT

A method and system for analyzing a target network relative to a background network of data using machine learning. The method includes extracting a first feature matrix from an adjacency matrix representative of the target network, extracting a second feature matrix from an adjacency matrix representative of the background network, generating a projection matrix based on the first and second feature matrices using a contrastive learning algorithm, generating a first contrastive matrix representation of the target network based on the projection matrix and the first feature matrix, generating a second contrastive matrix representation of the background network based on the projection matrix and the second feature matrix, and displaying a visualization of unique features of the target network relative to the background network based on the first contrastive matrix and the second contrastive matrix.

21 Claims, 11 Drawing Sheets

(56) References Cited

OTHER PUBLICATIONS

Kohler, S., et al., The Human Phenotype Ontology Project: Linking Molecular Biology and Disease through Phenotype Data, Nucleic Acids Research, 2014, 42, D966-D974.

Glueck, M., et al., PhenoBlocks: Phenotype Comparison Visualizations, IEEE Transactions on Visualization and Computer Graphics, 22(1), Jan. 2016, pp. 101-110.

Tantardini, M., et al., Comparing Methods for Comparing Networks, Scientific Reports, 9, 2019, 20 pgs.

Abid, A., et al., Exploring Patterns Enriched in a Dataset with Contrastive Principal Component Analysis, Nature Communications, 9, 2018, 7 pgs.

Grover, A., et al., node2vec: Scalable Feature Learning for Networks, KDD '16, Aug. 13-17, 2016, San Francisco, CA, pp. 855-864.

Zhang, Z., et al., Deep Learning on Graphs: A Survey, Dec. 11, 2018, arXiv:1812.04202, 15 pgs., [online] URL: https://www.google.com/url?sa=t&rct=j&q=&esrc=s&source=web&cd=2&cad=rja&uact=8&ved=2ahUKEwjRt7Lro9LnAhXNPn0KHQT0DacQFjABegQIAxAB&url=https%3A%2F%2Farxiv.org%2Fabs%2F1812.04202&usg=AOvVaw0PcRznPPC3WpxC_Wz44-FA.

Hamilton, W. L., et al., Inductive Representation Learning on Large Graphs, 31st Conference on Neural Information Processing Systems (NIPS 2017), Long Beach, CA, 11 pgs.

Chen, J., et al., FastGCN: Fast Learning with Graph Convolutional Networks via Importance Sampling, conference paper at ICLR, Jan. 30, 2018, 15 pgs.

Rossi, R. A., et al., Deep Inductive Graph Representation Learning, IEEE Transactions on Knowledge and Data Engineering, 14(8), Feb. 2018, 14 pgs.

Abid, A., et al., Contrastive Variational Autoencoder Enhances Salient Features, arXiv:1902.04601, Feb. 12, 2019, 17 pgs.

Fujiwara, T., et al., Supporting Analysis of Dimensionality Reduction Results with Contrastive Learning, IEEE Transactions on Visualization and Computer Graphics, 2019, 11 pgs.

Fujiwara, T., et al., A Visual Analytics System for Brain Functional Connectivity Comparison Across Individuals, Groups, and Time Points, 2017 IEEE Pacific Visualization Symposium (PacificVis), Apr. 18-11, 2017, Seoul, Korea, pp. 250-259.

Van den Elzen, S., et al., Reducing Snapshots to Points: A Visual Analytics Approach to Dynamic Network Exploration, IEEE Transactions on Visualizations and Computer Graphics 22(1), Jan. 2016, 10 pgs.

Kwon, O-H., et al., What Would a Graph Look Like in This Layout? A Machine Learning Approach to Large Graph Visualization, IEEE Transactions on Visualization and Computer Graphics, 24(1), Jan. 2018, pp. 478-488.

Przulj, N., et al., Modeling Interactome: Scale-Free or Geometric?, Bioinformatics, Dec. 12, 2004, 20(18), pp. 3508-3515.

Chu, X., et al., Cross-Network Embedding for Multi-Network Alignment, WWW'19, May 13-17, 2019, San Francisco, CA, 11 pgs.

\* cited by examiner

SYSTEM AND METHOD FOR CONTRASTIVE NETWORK ANALYSIS AND VISUALIZATION

BACKGROUND

Field

The present disclosure relates to data analysis, and more specifically, to systems and methods of automatically comparing and contrasting networks to identify patterns in data.

Related Art

In related art applications, data networks, defined as a collection of data nodes joined together in pairs by links or data connections, may be used to model various types of relationships in a real-world application. By analyzing an entire network, the related art may be able to uncover various important factors that might not be obvious in the individual relationships.

There are several approaches to network comparison described in the related art. For example, when two different networks have the same node-set and the pairwise correspondence between nodes is known, some related art techniques may compute a similarity between two networks (e.g., a Euclidean distance between two adjacency matrices). Additionally, when node-correspondence is not known or such correspondence does not exist, network-statistics based approaches may be used in the related art (e.g., the clustering coefficient, network diameter, or node degree distribution). Another related art technique involves using graphlets (e.g., small, connected, and non-isomorphic subgraph patterns in a complete graph of three nodes). In this related art approach, similarities between networks can be obtained by comparing the frequency of appearances of each graphlet in each network.

However, while these related art approaches may provide a similarity between different networks, each network comparison in the related art is only based on one selected measure (e.g., node degree). As a result, the related art measures do not provide sufficient comparisons of the network by other measures. Further, these related art approaches may only provide network-level similarities and cannot compare networks in more detailed levels (e.g., at the node-level). Without a detailed-level comparison, a user of these related art techniques may not be able to determine which parts of a network relate to a network's uniqueness.

SUMMARY OF THE DISCLOSURE

Aspects of the present application may include a method of analyzing a target network relative to a background network of data using machine learning. The method may include extracting a first feature matrix from an adjacency matrix representative of the target network, extracting a second feature matrix from an adjacency matrix representative of the background network, generating a projection matrix based on the first and second feature matrices using a contrastive learning algorithm, generating a first contrastive matrix representation of the target network based on the projection matrix and the first feature matrix, generating a second contrastive matrix representation of the background network based on the projection matrix and the second feature matrix, and displaying a visualization of unique features of the target network relative to the background network based on the first contrastive matrix and the second contrastive matrix.

Additional aspects of the present application may include a non-transitory computer readable medium encoded with instructions for making a computing device execute a method of analyzing a target network relative to a background network of data using machine learning. The method may include extracting a first feature matrix from an adjacency matrix representative of the target network, extracting a second feature matrix from an adjacency matrix representative of the background network, generating a projection matrix based on the first and second feature matrices using a contrastive learning algorithm, generating a first contrastive matrix representation of the target network based on the projection matrix and the first feature matrix, generating a second contrastive matrix representation of the background network based on the projection matrix and the second feature matrix, and displaying a visualization of unique features of the target network relative to the background network based on the first contrastive matrix and the second contrastive matrix.

Further aspects of the present application may include a computing device including a storage device and a processor. The storage device may store network data associated with a target network and a background network. The processor may be encoded to execute a method of automatically analyzing the target network relative to the background network of data using machine learning. The method may include extracting a first feature matrix from an adjacency matrix representative of the target network, extracting a second feature matrix from an adjacency matrix representative of the background network, generating a projection matrix based on the first and second feature matrices using a contrastive learning algorithm, generating a first contrastive matrix representation of the target network based on the projection matrix and the first feature matrix, generating a second contrastive matrix representation of the background network based on the projection matrix and the second feature matrix, and displaying a visualization of unique features of the target network relative to the background network based on the first contrastive matrix and the second contrastive matrix.

Further aspects of the present application may include a computing device for automatically analyzing the target network relative to the background network of data. The computing device may include storage means for storing network data associated with a target network and a background network, means for extracting a first feature matrix from an adjacency matrix representative of the target network, means for extracting a second feature matrix from an adjacency matrix representative of the background network, means for generating a projection matrix based on the first and second feature matrices using a contrastive learning algorithm, means for generating a first contrastive matrix representation of the target network based on the projection matrix and the first feature matrix, means for generating a second contrastive matrix representation of the background network based on the projection matrix and the second feature matrix, and means for displaying a visualization of unique features of the target network relative to the background network based on the first contrastive matrix and the second contrastive matrix.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
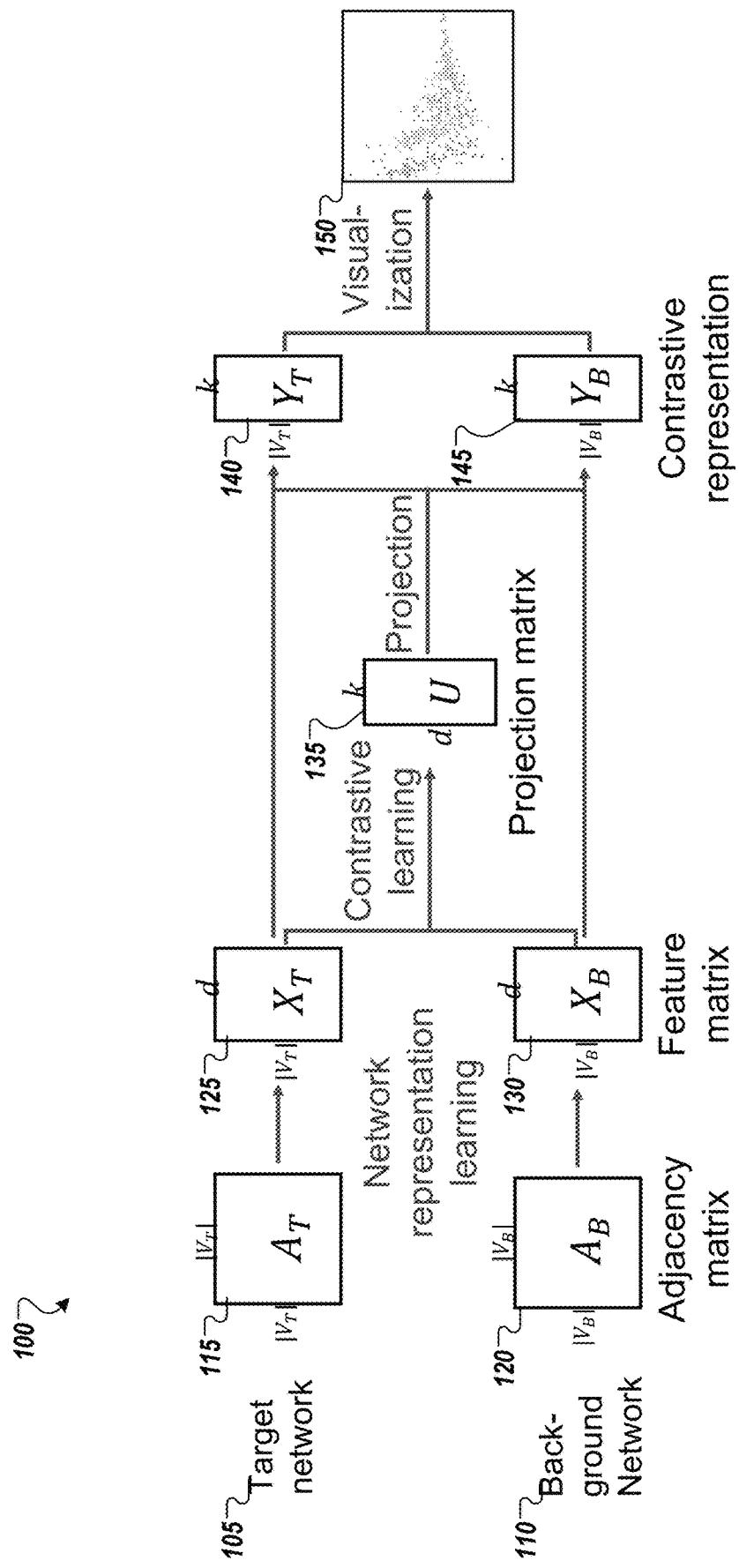
FIG. 1 illustrates a schematic representation of a contrastive network analysis process in accordance with example implementations of the present application.

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or operator control over certain aspects of the implementation, depending on the desired implementation of one of ordinary skill in the art practicing implementations of the present application. Further, sequential terminology, such as "first", "second", "third", etc., may be used in the description and claims simply for labeling purposes and should not be limited to referring to described actions or items occurring in the described sequence. Actions or items may be ordered into a different sequence or may be performed in parallel or dynamically, without departing from the scope of the present application.

In the present application, the term "computer readable medium" may include a local storage device, a cloud-based storage device, a remotely located server, or any other storage device that may be apparent to a person of ordinary skill in the art.

As discussed above, a data network (e.g., a collection of nodes joined together in linked pairs) is frequently used in the related art to model various types of relationships in real-world applications. This type analysis is applied to networks in many different disciplines, including social networks in sociology, cellular networks in biology, communication networks in software engineering, and many more. This type of network analysis may allow discovery of various important factors that might not be obvious in basic relationships. For example, social networks derived from social media sites (e.g., short blog sites, message casting sites, image sharing sites, etc.) may be used to identify influential people fostering critical public opinions.

Additionally, in some disciplines, different networks may be analyzed to identify differences between networks or certain measures of uniqueness may be detected in a network when compared with another network. For instance, a neuroscientist may study effects of Alzheimer's disease on a brain by comparing the brain network of a patient of Alzheimer's disease with the brain network of a healthy subject.

Further, by examining collaboration networks of researchers in different fields, a network analyst may wish to reveal unique ways of collaborating in a certain field. Another example may relate to analyzing an ontology network of human phenotypes, which are "observable and measurable traits of patient morphology (e.g., enlarged heart), physiology (e.g., seizures), or behavior (e.g., depression)." By comparing the ontology subnetworks which relate to a specific disease (e.g., physiological changes, physical symptoms, or behavioral symptoms detected in diagnosed persons), researchers can better understand each disease's characteristics, such as concluding that wider variety of phenotypes are related to one disease. Thus, determining what makes a network unique can contribute to a greater understanding of the network.

As discussed above, several approaches of machine learning based network comparison in the related art can be used, including computation of network similarities, network-statistics based approaches (e.g., the clustering coefficient, network diameter, or node degree distribution), and graphlets (e.g., small, connected, and non-isomorphic subgraph patterns in a graph (e.g., the complete graph of three nodes)). However, these related art approaches only compare networks based on a single selected measure (e.g., node degree). As a result, the selected measures can produce insufficient comparisons. Further, these related art approaches only provide network-level similarities and cannot compare networks in more detailed levels (e.g., at the node-level). Without a detailed-level comparison, a user may not be able to determine which parts of a network relate to its uniqueness.

Thus, example implementations of the present disclosure include a method for using machine learning to compare two different networks where the node-correspondence may be unknown by utilizing the concept of contrastive learning. As described in example implementations of the present disclosure, contrastive learning is an analysis approach for high-dimensional data, which aims to discover patterns enriched in (e.g., unique to) one dataset relative to another data set. By applying this concept to network analysis, example implementations of the present disclosure may reveal unique patterns in one network by contrasting a target network with another network in a comprehensible (e.g., using multiple measures to capture the network characteristics) and detailed (e.g., analyzing a node or subgraph level) manner. In other words, by comparing two networks, the factors or aspects of the network unique can be identified.

However, as networks are generally represented by an adjacency matrix, row and column corresponding to a network node, with each cell representing a connection between nodes, contrastive learning may not be easily applied to network analysis. Instead, feature matrices must be extracted from each network using network representation learning to perform contrastive learning. Thus, to achieve such contrastive analysis, example implementations of the present disclosure may utilizes a contrastive learning method together with network representation learning. Further, unlike many other machine learning methods for network analysis (e.g., node2vec and graph neural networks), example implementations of the present application may also offer interpretability in analysis results. With the interpretability and interactive visualizations, example implementations of the present disclosure may also provide a functionality to help understand why a certain pattern may be found in one network.

FIG. 1 illustrates a schematic representation 100 of a contrastive network analysis process in accordance with example implementations of the present application. In the illustrated process, a target network 105 is contrasted with a background network 110. Specifically, the process generates contrastive representations 140, 145 from the target network 105 and the background network 110, respectively. These contrastive representations may reveal patterns that are specific to the target network 105 when compared to the background network 110. In some example implementations, the contrastive representations 140, 145 may be obtained via the following steps.

First, each network (target network 105 and background network 110) is represented as an adjacency matrix or adjacency list (adjacency matrix 115 corresponding to target network 105 and adjacency matrix 120 corresponding to background network 110). Each adjacency matrix 115, 120 contains information of linked node pairs with the values $|V_T|$ and $|V_B|$ representing the numbers of nodes within target network 105 and background network 110, respectively. However, each adjacency matrix or adjacency list 115, 120, may not itself have features that can be used for contrastive learning. Thus, a feature matrix may be generated from each adjacency matrix 115, 120 associated with the target network 105 and background network 110 using network representation learning. For example, feature matrix 125 may be generated from the adjacency matrix 115 associated with the target network 105 as the target. Further, feature matrix 130 may be generated from the adjacency matrix 120 associated with the background network 110. As illustrated in FIG. 1, each project matrix 125, 130 has dimensions corresponding to the number of nodes within the underlying network (e.g., target network node number $|V_T|$ and background network node $|V_B|$) by the number of features obtained with network representation learning (d).

Any inductive network representation learning method (e.g., algorithms such as GraphSAGE, FastGCN, or any other representation learning method that might be apparent to a person of ordinary skill in the art) may be used for generating the feature matrices 125, 130.

Figure 3A:
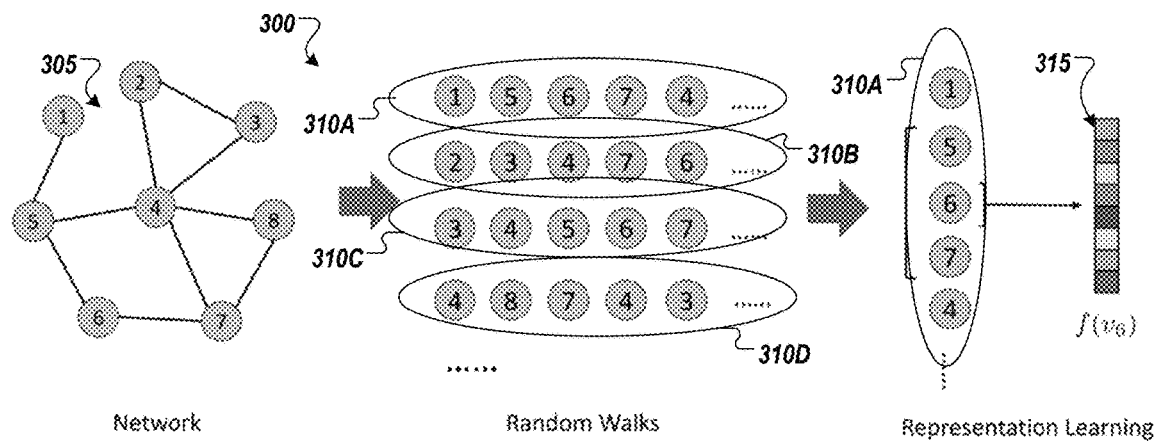
FIGS. 3A and 3B illustrate schematic representations of different network representation learning methods that may be used in example implementations of the present disclosure.
Figure 3B:
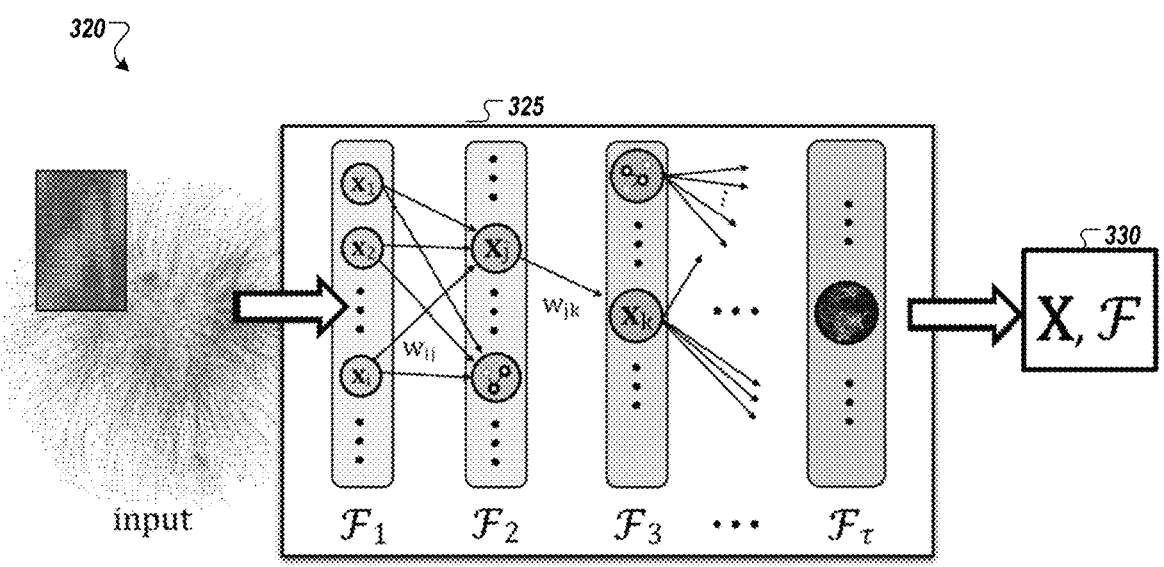

Further, in some example implementations, the selected inductive network representation learning method may be a method that can generate interpretable features (e.g., algorithms such as DeepGL or any other representation learning method that might be apparent to a person of ordinary skill in the art). FIGS. 3A & 3B discussed below show schematic representations of different network representation learning methods that may be used in example implementations of the present disclosure.

From the obtained feature matrices 125, 130, a projection matrix 135 may be generated by applying contrastive learning. The projection matrix 135 may be a parametric mapping from the original feature dimensions to a lower embedding space. Within the projection matrix, the dimension k may be the number of dimensions of the lower dimensional representation obtained with contrastive learning.

In some example implementations, any contrastive learning method that may provide a projection matrix may be used (e.g., algorithms such as contrastive PCA, contrastive variational auto encoder, or any other any other contrastive learning method that might be apparent to a person of ordinary skill in the art). In some example implementations, contrastive PCA may be used to provide the features' contributions to the projection matrix 135. With contrastive PCA, features' contributions may be obtained by referring to contrastive principal component loadings. Alternatively, contrastive PCA may be replaced with another method that can provide features' contributions if such a method may be developed in the future.

By multiplying each feature matrix 125, 130 (e.g., feature matrix 125 generated from the target network 105 or feature matrix 130 generated from background network 110) by the projection matrix 135, we can obtain contrastive representation matrices 140, 145 respectively. Matrix 140 is representative of the projection matrix 135 being multiplied by the feature matrix 125 associated with the target network 105. Further, matrix 145 is representative of the projection matrix 135 being multiplied by the feature matrix 130 associated with the background network 110.

These contrastive representation matrices 140, 145 may then be visualized for interactive analysis as visualization 150. Specific examples of the visualization 150 and its manipulation are discussed in greater detail below with respect to FIGS. 4-9.

Figure 2:
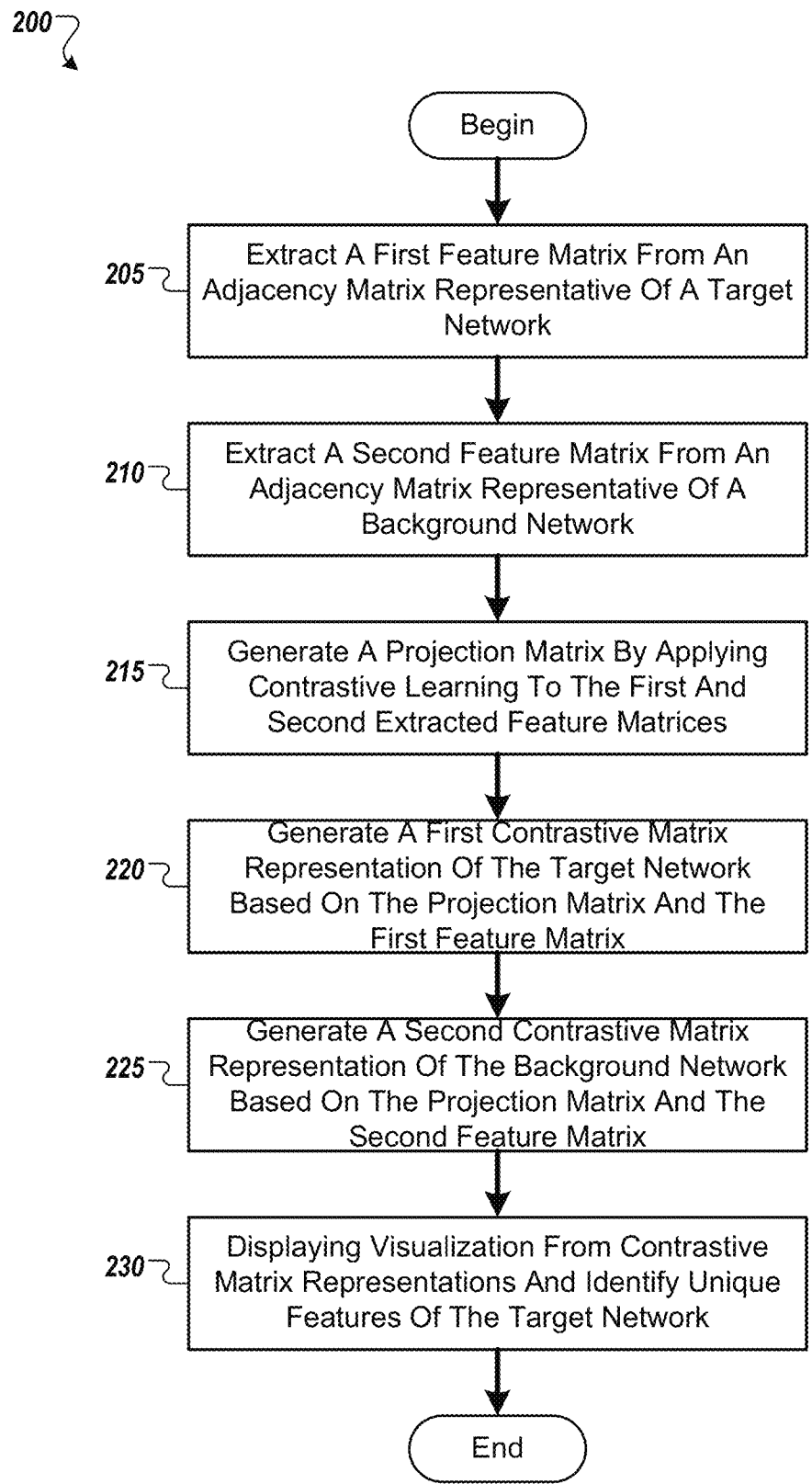
FIG. 2 illustrates a flowchart of a process for contrastively analyzing a pair of networks in accordance with example implementations of the present application.

FIG. 2 illustrates a flowchart of a process 200 for contrastively analyzing a pair of networks in accordance with example implementations of the present application. The process 200 may be performed by one or more computing devices (e.g., computing device 1205 of computing environment 1200 of FIG. 2). In process 200, a target network represented by an adjacency matrix, which comprises rows and columns representative of network nodes and individual cells representative of network connections, may be used to generate a first feature matrix at 205. Specifically, the adjacency matrix representing the target network (e.g., the network for which comparative analysis is desired) may be subject to a network representation learning algorithm to extract network features to generate a first feature matrix. The network representation learning algorithm (e.g., a DeepGL algorithm or other network representation learning algorithm that might be apparent to a person of ordinary skill in the art) may compute multiple feature metrics associated with the adjacency matrix to represent the features of the target network. Computed metrics may include one or more of: node degree for each node, page rank for each node, network centrality for each node, mean page rank around neighbors, max value of neighbors, and network centrality for each node. In some example implementations, the computed metrics may be calculated for each node and for each neighbor, and for each neighbor of a neighbor (a 2-hop neighbor) and so on to calculate all of the metrics for multiple degrees or hops of neighbors within the target network. This may produce a first feature matrix having semantically meaningful representations of the target network.

Similarly, at 210 a background network represented by an adjacency matrix, which comprises rows and columns representative of network nodes and individual cells representative of network connections, may be used to generate a second feature matrix. Specifically, the adjacency matrix representing the background network (e.g., the network to which the target network is to be comparatively analyzed) may be subject to a network representation learning algorithm to extract network features to generate a first feature matrix. Again, the network representation learning algorithm (e.g., a DeepGL algorithm or other network representation learning algorithm that might be apparent to a person of ordinary skill in the art) may compute multiple feature metrics associated with the adjacency matrix to represent the features of the background network. Computed metrics may include one or more of: node degree for each node, page rank for each node, network centrality for each node, mean page rank around neighbors, max value of neighbors, and network centrality for each node neighbor and any other metric that might be apparent to a person of ordinary skill in the art. In some example implementations, the computed metrics may be calculated for each node and for each neighbor, and for each neighbor of a neighbor (a 2-hop neighbor) and so on to calculate all of the metrics for multiple degrees or hops of neighbors within the background network. This may produce a second feature matrix having semantically meaningful representations of the background network.

At 215, the first feature matrix representative of the target network and the second feature matrix representative of the background network may be subject to a contrastive learning algorithm to generate a projection matrix. For example, a contrastive learning algorithm (e.g., contrastive PCA algorithm or any other contrastive learning algorithm that might be apparent to a person of ordinary skill in the art) may compare the first feature matrix to the second feature matrix to create a projection matrix that comprises the unique features of the target network that are not found in the background network.

At 220, a contrastive representation matrix of the target network may be generated by multiplying the projection matrix by the first feature matrix that was representative of the target network. Similarly, at 225 a contrastive representation matrix of the background network may be generated by multiplying the projection matrix by the second feature matrix that was representative of the background network.

At 230, the contrastive representation matrices of the target network and the background network may be displayed in a visualization discussed below with respect to FIGS. 4-10 to facilitate contrastive analysis of the target network. By detecting uniqueness in the target network, the unique features of the target network may be detected, recognized and studied.

In some example implementations, the target network may be a neuron network representation or brain scan image of a human patient brain at a current time or a specific time (e.g., after application of a treatment) and the background network may be a neuron network representation or brain scan image of the same patient taken at a previous time before the current time or at a prior time (e.g., prior to application of the treatment). In this implementation, the resulting visualization may illustrate whether the treatment has been effective in treating the patient's neurological symptom or disorder by visualizing the unique features of the target network (e.g., the patient's neuron network representation or brain scan image). This may have powerful visualizations as part of neurological research and treatment (e.g., Alzheimer's research or other neurological disorder research).

In other example implementations, the target network may be a social graph or collaboration network (a network representation of collaborators or researchers working in a specific research domain) at a current time and the background network may be the social graph or collaboration network at a previous time in the past. In this implementation, the resulting visualization may illustrate changes in research or collaboration teams over time, which can be indicative of changes in research interest and other factors affecting collaboration in the specific research domain.

In other example implementations, the target network may be a network representation of phenotypic features of one biological species and the background network may be a network representation of phenotypic features of another related biological species. In this implementation, the resulting visualization may illustrate differences in closely related species to allow enhanced species differential study.

In still other example implementations, the target network may be a network representation of links between symptoms or morphologies found in patients diagnosed with a first disease and the background network may be a network representation of links between symptoms or morphologies found with a different disease. The resulting visualization may identify unique morphologies associated with the first disease to allow better diagnosis based on recognized symptom or morphology clusters.

In a further example implementation of the present disclosure, contrastive network analysis may be used to refine a data network modeling platform or application. For example, a network modeling platform or application may be used to generate a model of a real world network. Once the model has been generated, the real world network (e.g., a biological population network, a computing network, an electrical network, or any other real world network that might be apparent to a person of ordinary skill in the art) being modeled may be used as the target network and the generated model may be used as a background network in a contrastive network analysis process in accordance with the present application. The result of the contrastive network analysis would produce features of the real world network that are unique compared to the model. The model can then be updated to incorporate the unique features of the real world network that were not accounted for in the model.

These example implementations are not exhaustive of the possible networks that may be used with the methods and systems described herein and the systems and methods described herein may be applied to compare other types of networks to identify unique features or to compare the same network over time to identify changes.

FIGS. 3A and 3B illustrate schematic representations of different network representation learning methods that may be used in example implementations of the present disclosure. FIG. 3A illustrates a schematic representation 300 of network representation learning methods that rely on "Random Walk" algorithms (e.g., node2vec or other "Random Walk" algorithms that might be apparent to a person of ordinary skill in the art). As illustrated, this type of network representation analyzes a network (305) of interconnected nodes (circles 1-8) and generates a series of linked node sequences (310A-310D). Each linked node sequence (310A-310D) may be generated by randomly selecting one node of the network 305 and randomly following (e.g., walking) the links connecting to the other nodes. From each linked node sequence, a feature vector 315 may be extracted by extracting features from each node and sequencing the extracted features based on the linked node sequence.

However, the extracted features from one node may not have any semantic relationships to extracted features of a subsequent node. If the extracted features from the nodes do not have any semantic relationship, using the resulting feature vector may not have any meaning, making interpretation from the features difficult.

FIG. 3B includes a schematic representation 320 of inductive network representation learning methods that can generate interpretable features. In this method, a matrix 325 of feature weights where $w_{ij}$ (or $W_{ij}$) is the weight between the feature vectors $x_i$ and $x_j$ generated from node sequences. As illustrated, the matrix 325 has the constraint that i<j<k and $x_i$, $x_j$, and $x_k$ are each successively deeper. Each feature layer $F_h \in F$ defines a set of unique relational functions $F_h = \{***, f_{k^*}***\}$ of order h (depth). Further, each $f_k \in F_h$ denotes a relational function. Further, F may be defined by equation 1 below and |F| may be defined by equation 2 below:

$$F = F_1 \cup F_2 \cup \ldots \cup F_\tau \quad \text{(Equation 1);}$$

$$|F| = |F_1| + |F_2| + \ldots + |F_\tau| \quad \text{(Equation 2).}$$

Additionally, the layers may be ordered where $F_1 < F_2 < \ldots < F_\tau$ such that if i<j, then $F_j$ is said to be a deeper layer compared to Fi.

Using this framework, an inductive network representation learning method may learn relational functions that may correspond to increasingly higher-order subgraph or subnetwork features based on a set of initial lower-order (base) subgraph or subnetwork features. Thus, similar to filters used in Convolutional Neural Networks (CNNs), this inductive network representation learning method may be similarly understood, with simple filters being replaced by lower-order subgraphs being combined in various ways to capture higher-order subgraph patterns of increasingly complexity at each successive layer.

In this manner, inductive network representation learning methods such as illustrated in FIG. 3B may learn both relational features and base features to create the feature matrix 330 that will be associated with the respective base and target networks, which may allow interpretable features to be generated.

Figure 4:
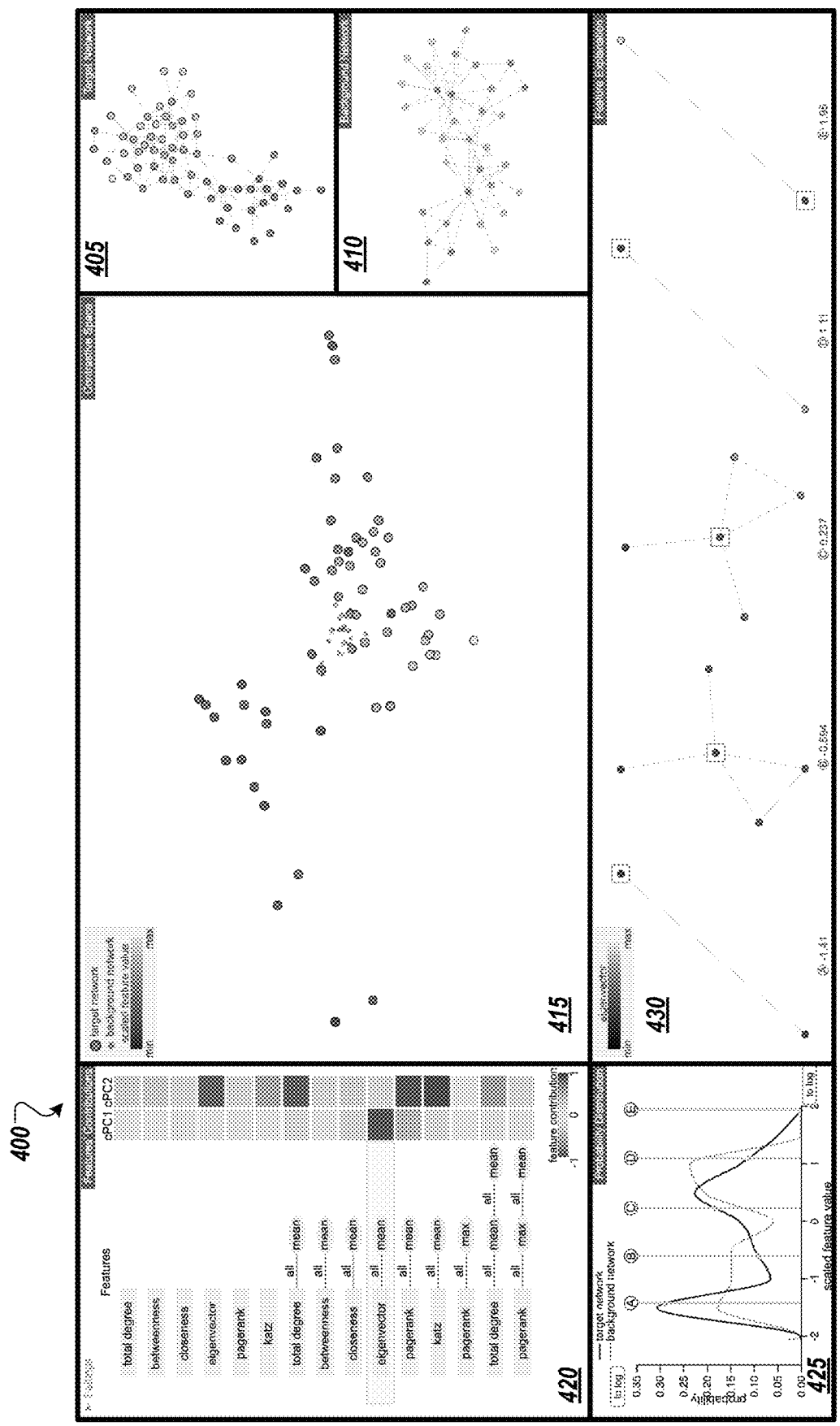
FIG. 4 illustrates a User interface that may provide a visualization of contrastive network analysis in accordance with example implementations of the present disclosure.

FIG. 4 illustrates a user interface 400 that may provide a visualization of contrastive network analysis in accordance with example implementations of the present disclosure. The user interface 400 may be displayed on a display device of a computing device (e.g., computing device 1205 of computing environment 1200 of FIG. 12). For example, the user interface 400 may be displayed on a monitor, TV screen, laptop screen, tablet screen, or any other display device. Further, the user interface 400 may be displayed on a touch screen that provides direct user interaction or a non-touch screen device requiring user input device (e.g., a mouse, track ball, touch pad, joystick, keyboard, or any other user input device that might be apparent to a person of ordinary skill in the art).

As illustrated, the user interface 400 may have a number of subsections 405-430 that provide information about the contrastive network analysis in an interactive manner. For example, the user interface 400 may include network layout interfaces 405 and 410 that provide schematic overviews of the target and background networks. Specifically, target network layout interface 405 provides a graphical representation of the nodes of the target network being analyzed. Further, the background network layout interface 410 provides a graphical representation of the nodes of the background network being compared to the target network. The target and background network layout interfaces 405, 410 are discussed in greater detail below with respect to FIG. 5.

Further, the user interface 400 may also include a contrasting representation interface 415 which overlays the graphical representations of the target and background networks to visualize the results of contrastive representation learning produced through the contrastive network analysis process according to example implementations of the present disclosure described above with respect to FIG. 1. The contrastive representation interface 415 is discussed in greater detail below with respect to FIG. 6.

Additionally, the user interface 400 may include a features contribution interface 420 that provides definitions of the features stored in the feature matrix that was obtained through the network representation learning process described above with respect to FIG. 1. With this visualization, a user may see which features have highly contributed to the uniqueness of a target network. In other words, the user may determine which of the network features make the target network unique because they are not found in the background network. The features contribution interface 420 is discussed in greater detail below with respect to FIG. 7.

Still further, the user interface 400 may also include a probability distribution interface 425 and a feature explanation interface 430. The probability distribution interface 425 may show probability distributions of values of a selected feature of the target and background networks based on selections from the features contribution interface 420. Further, each node that has the selected value from the features contribution interface 420 may be visualized in the feature explanation interface 430. The probability distribution interface 425 and the feature explanation interface 430 are discussed in greater detail below with respect to FIGS. 9 and 10 respectively.

Figure 5:
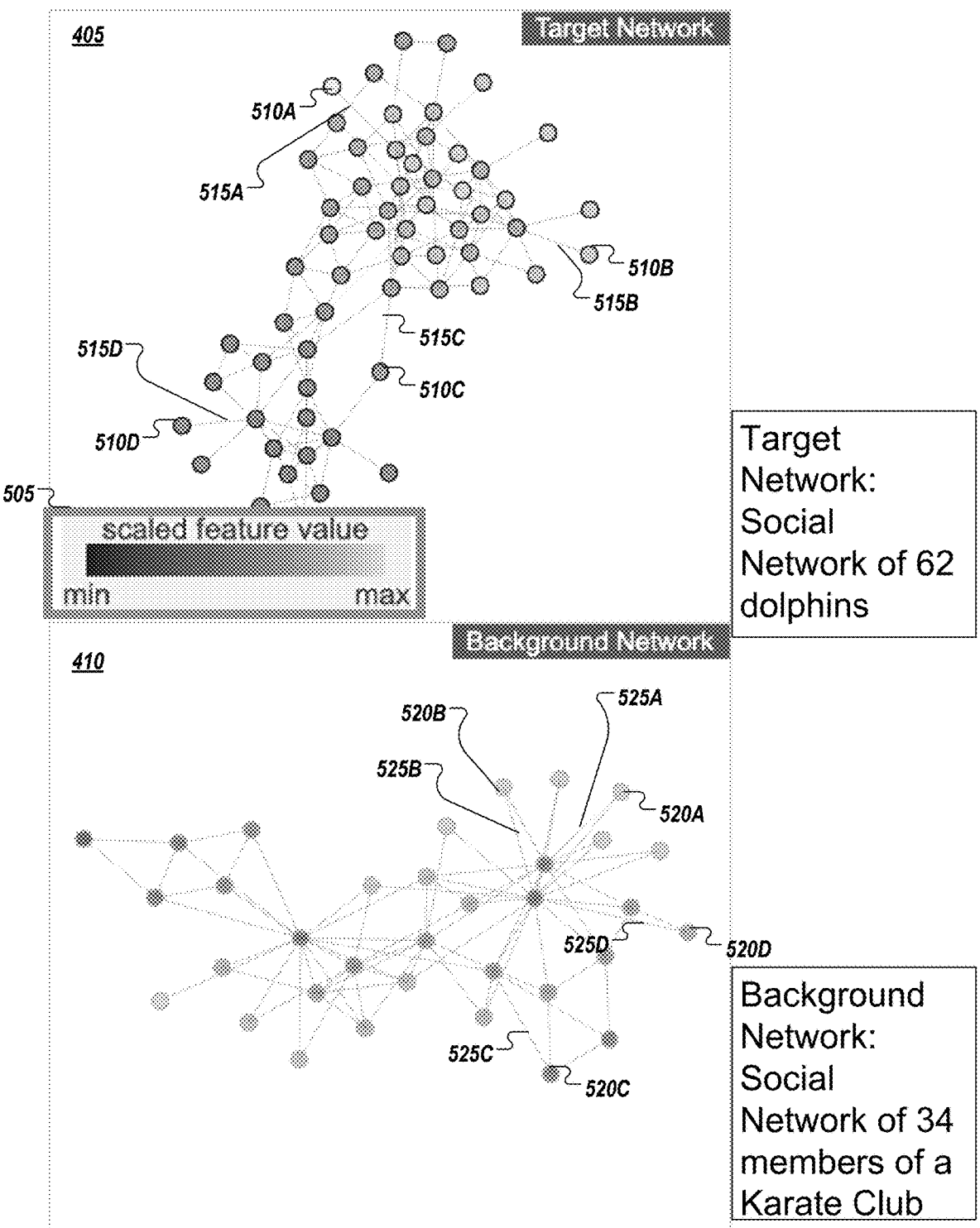
FIG. 5 illustrates an annotated version of the target and background network layout interfaces of the User interface of FIG. 4.

FIG. 5 illustrates an annotated version of the target and background network layout interfaces 405, 410 of the user interface 400 of FIG. 4. In FIG. 5, a legend 505 has been added for explanatory purposes. For purposes of explanation, the target network illustrated in the target network layout interface 405 is a social network of 62 dolphins in a marine pod being studied by a marine biologist. As illustrated, each dolphin is represented by a dot (e.g., 510A-510D) having a black parameter and an interior having a color or shade representative of a scaled value of a network feature. As illustrated, a dark color or shade dot (e.g., 510C & 510D) may represent minimum or small values of the scaled feature and a light color or shade dot (510A & 510B) may represent maximum or large values of the scaled feature. The links (e.g., 515A-515D) between the nodes represent connections or interactions between the dolphins.

For purposes of explanation, the background network illustrated in the background network layout interface 410 is a social network of 34 members of a karate club. As illustrated, each karate club member is represented by a dot (e.g., 520A-520D) having a white parameter and an interior having a color or shade representative of a scaled value of a network feature. As illustrated, a dark color or shade dot (e.g., 520C & 520D) may represent minimum or small values of the scaled feature and a light color or shade dot (e.g., 520A & 520B) may represent maximum or large values of the scaled feature. The links (e.g., 525A-525D) between the nodes represent connections or interactions between karate club members.

Figure 6:
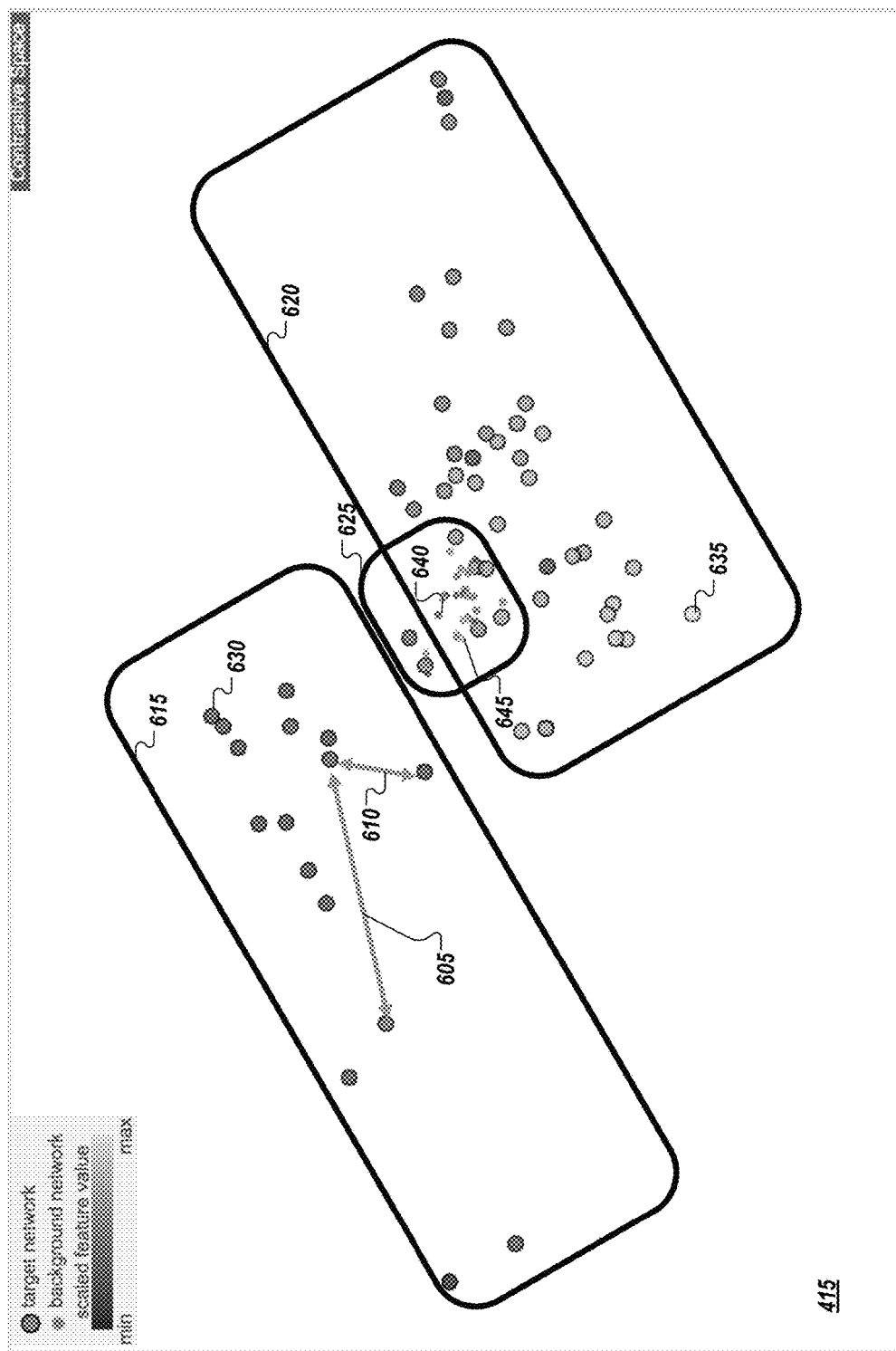
FIG. 6 illustrates an annotated version of the contrastive representation interface of the User interface of FIG. 4.

FIG. 6 illustrates an annotated version of the contrastive representation interface 415 of the user interface 400 of FIG. 4. In FIG. 6, arrows (e.g., 605 & 610) representative of node proximity, which may be representative of node similarity, have been added. Additionally, boxes 615-620 have been added to illustrate contrastive space of the target network and background network. Further, within the contrastive representation interface 415, both the target network and the background network are illustrated. As discussed above, the target network is a social network of 62 dolphins in a marine pod being studied by a marine biologist. As illustrated, each dolphin is represented by a dot (e.g., 630, 635) having a black parameter and an interior having a color or shade representative of a scaled value of a network feature. Further, the background network illustrated is a social network of 34 members of karate club. As illustrated, each karate club member is represented by a dot (e.g., 640, 645) having a white parameter and an interior having a color or shade representative of a scaled value of a network feature. As illustrated, a dark color or shade dot (e.g., 630, 640) may represent minimum or small values of the scaled feature and a light color or shade dot (e.g., 635 & 640) may represent maximum or large values of the scaled feature. From the contrastive representation interface, a user may observe whether nodes of the target network (e.g., 630, 635) have a specific pattern when compared to the nodes (e.g., 640, 645) of the background network and which target network's nodes have differences from which background network's nodes. For example, as shown in FIG. 6, while the background network's nodes (e.g., 640, 645) are placed only around the center (box 625), the target network's nodes (e.g., 630, 635) are more widely distributed in both x- and y-directions (boxes 615, 620).

Figure 7:
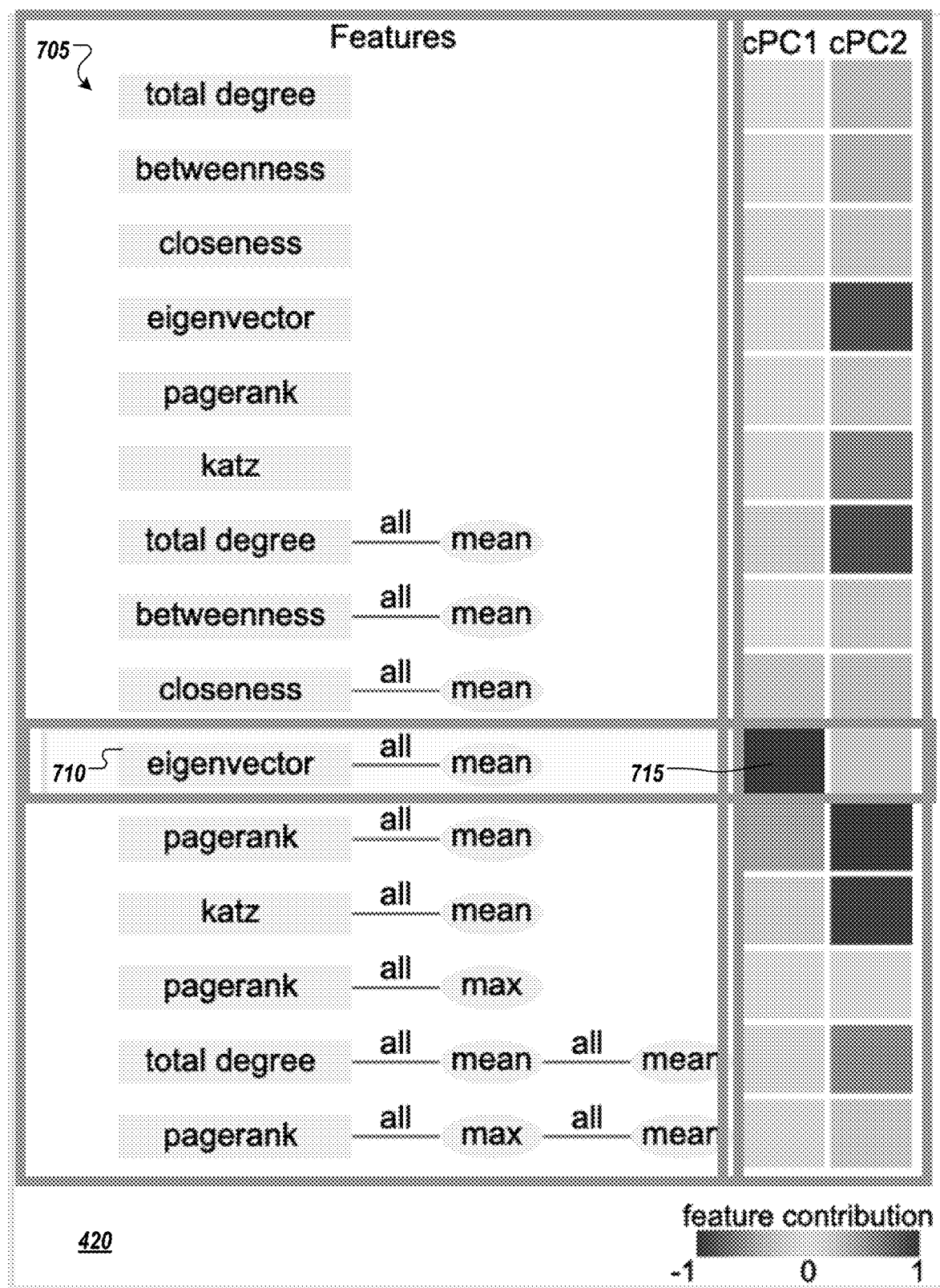
FIG. 7 illustrates an annotated version of features contribution interface of the User interface of FIG. 4.

FIG. 7 illustrates an annotated version of features contribution interface 420 of the user interface 400 of FIG. 4. As illustrated, the features contribution interface 420 may show a list of feature definitions 705 corresponding to the feature matrix's rows obtained with the step of network representation learning process described above with respect to FIG. 1. Additionally, by using a divergent color or shade map, the contributions of features obtained from the contrastive learning may be shown. With this features contribution interface 420, features which have highly contributed to the uniqueness of a target network may be shown with darker or stronger features. For example, as shown in FIG. 7, the highlighted feature 710 color has a high absolute feature contribution, as indicated with dark square 715 on the left. Also, example implementations of the present disclosure may provide intuitive representations of a feature definition because many of network representation learning methods, including DeepGL, may generate a complicated feature that is computed with each node's neighbors' centrality (or base feature).

Figure 8:
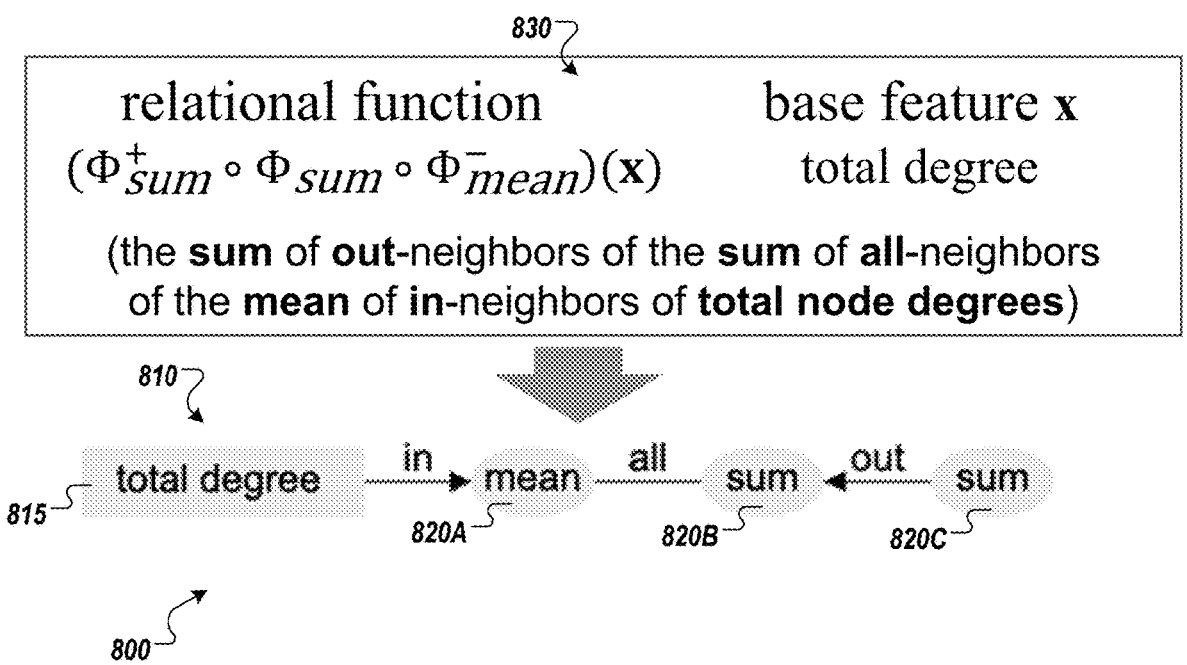
FIG. 8 illustrates a graphical representation of the generation of complicated features shown in the features contribution interface in accordance with example implementations of the present application.

Further, FIG. 8 illustrates a graphical representation 800 of the generation of complicated features shown in the features contribution interface 420 in accordance with example implementations of the present application. As shown in FIG. 8, for each feature, a (directional) line 810 may be used to show neighbor types (in-, out-, or all-neighbors) with rectangles 815 being used to show a base feature (e.g., total node degree) and circles 820A, 820B, 820C being used to show a function (e.g., mean, sum) used to summarize the neighbors' values. For reference, the relationship function 830, which the line 810 graphically represents, (e.g., the relationship between the nodes of respective networks and the base function) is illustrated. For example, in FIG. 8, the relationship function 830 illustrates that the associated line 810 represents the sum of all out-neighbors that is the sum of all neighbors of the mean of the in neighbors for the total node degrees. As illustrated, the line representation 810 may be more easily understood by a user as compared to the relationship function 830. Though the total degree base feature is represented by the rectangle in FIG. 8, base features may be shown using similar diagrams as may be apparent to a person of ordinary skill in the art.

Figure 9:
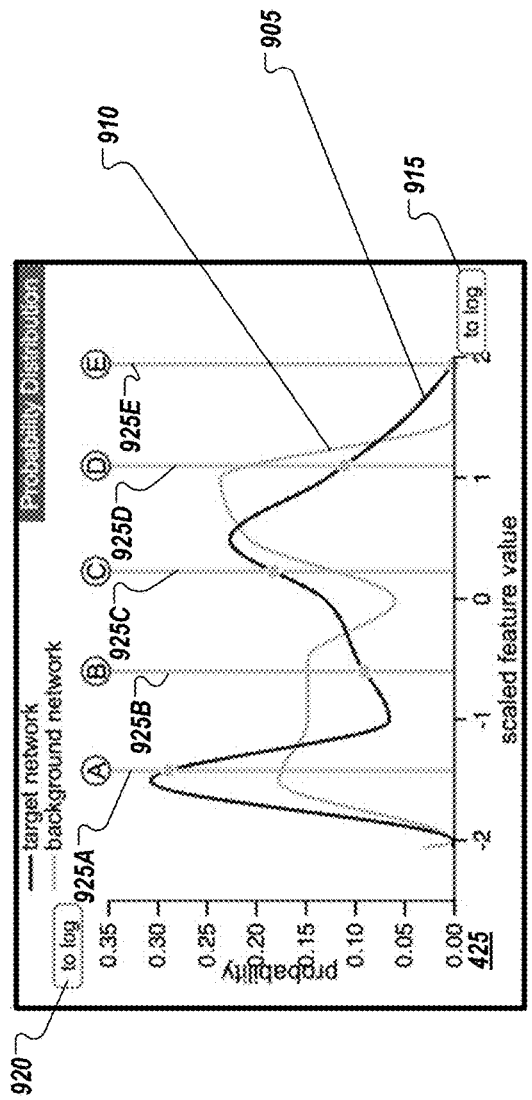
FIG. 9 illustrates an enlarged version copy of the probability distribution interface of the User interface of FIG. 4.

FIG. 9 illustrates an enlarged version copy of the probability distribution interface 425 of the user interface 400 of FIG. 4. As illustrated in FIG. 9, the probability distribution interface 425 shows the target network probability distribution curve 905 and background network probability distributions curve for network feature selected from the features contribution interface 420 described above.

As illustrated, for a feature selected from the features contribution interface 420, example implementations of the process of the present disclosure may automatically select several representative feature values (e.g., quantiles {A, B, C, D, E}), as shown with pink vertical lines 925A, 925B, 925C, 925D, 925E in FIG. 9. The probability distribution interface 425 also includes a pair of radio controls 915, 920 that can be used to toggle the displayed curves to be normalized, logarithmically scaled, or scaled with combination of normalized and logarithmically scaled.

Figure 10:
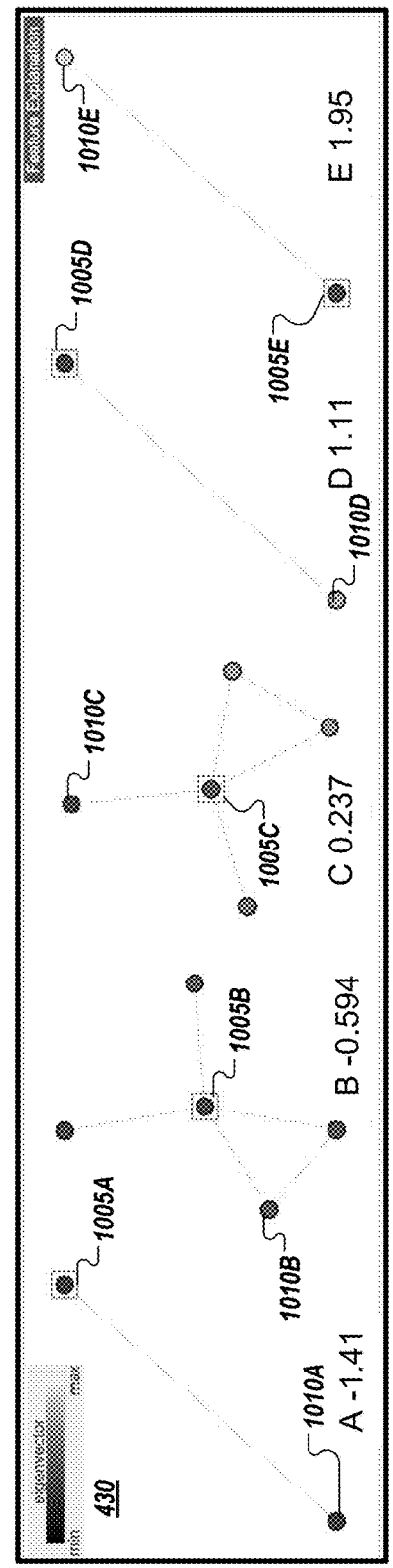
FIG. 10 illustrates an enlarged copy of the feature explanation interface of the User interface of FIG. 4.

FIG. 10 illustrates an enlarged copy of the feature explanation interface 430 of the user interface 400 of FIG. 4. The feature explanation interface 430 may provide a supplemental visualization to help understand how the feature value of each node is obtained. As explained above, for a feature selected from the features contribution interface 420, example implementations of the process of the present disclosure may automatically select several representative feature values (e.g., quantiles {A, B, C, D, E}). Then, as shown in FIG. 10, each node having the selected value may be visualized in the feature explanation interface 430 with a box 1005A-1005E surrounding colored or shaded dots. Example implementations of the present application may also visualize all the neighbors (e.g., dots illustrated in FIG. 10 and selectively numbered with reference numeral 1010A-1010E) related to computing the feature value. The dots (e.g., 1010A-1010E) representative of the neighbors and the nodes may be shaded or colored based on the computed value of the feature illustrated. For example, darker dots (e.g., 1010A, 1010B, 1010C) may be representative of smaller values and lighter dots (e.g., 1010D, 1010E) may be representative of larger values.

Figure 11:
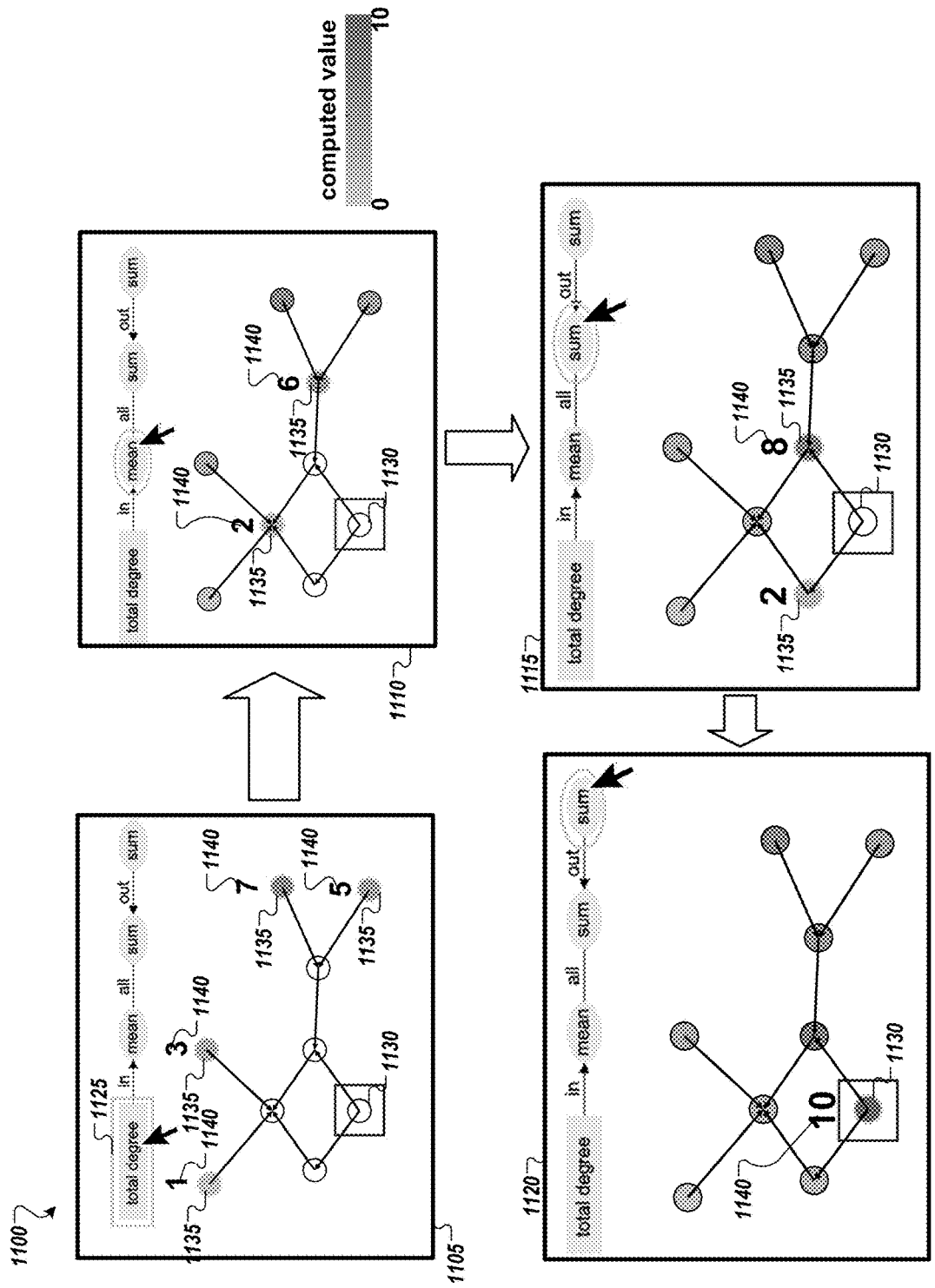
FIG. 11 illustrates a schematic representation of a process of computing the feature value of a selected node step-by-step in accordance with example implementations of the present application.

FIG. 11 illustrates a schematic representation 1100 of a process of computing the feature value of a selected node 1130 step-by-step in accordance with example implementations of the present application. As shown at 1105, when the user hovers over the base feature name 1125, the base feature values of the related nodes 1135 are represented by displayed numerals 1140. Similarly, as shown in 1110, when hovering over the function name (e.g., mean), the related nodes 1135 to the mean function and the computed values 1140 are displayed. Further, as shown in 1115, hovering over the function name (e.g., all sum) causes related nodes 1135 to the all sum function and the computed values 1140 to be displayed. Additionally, as shown in 1120, hovering over the function name (e.g., out sum) causes related nodes 1135 to the out sum function and the computed values 1140 to be displayed.

Applying the individual steps (e.g., 1105-1120) shown in FIG. 11, the feature value may be calculated. First, in 1105 the base feature (i.e., total node degree) is selected and the visualization colors the nodes 1135 that have the total node degree, which is related to computation of the feature value of the node 1130 indicated with the blue square. As shown in 1105, these related nodes are highlighted with light outer-ring colors. The white nodes (unlabeled) are not used for the computation at this stage. Next, in 1110, when the mean function name is selected, the related nodes 1135 are highlighted and colored based on the mean value of the total node degrees of their in-neighbors. In 1115 and 1120, the remaining white nodes are colored in the similar manners based on the selected functions.

Additionally, in some example implementations, all interfaces 405-430 of the UI 400 may support brushing-and-linking among the other visualizations 405-430. For example, the values of the selected feature in the feature contribution interface 420 may be shown as colors of nodes in target network interface 405, background network interface 410 and the contrastive representation interface 415. Since contrastive learning can find specific patterns in one network by comparing with another network, the user interface 400 described above may allow a user to switch the target and background networks used for contrastive network representation learning.

EXAMPLE COMPUTING ENVIRONMENT

Figure 12:
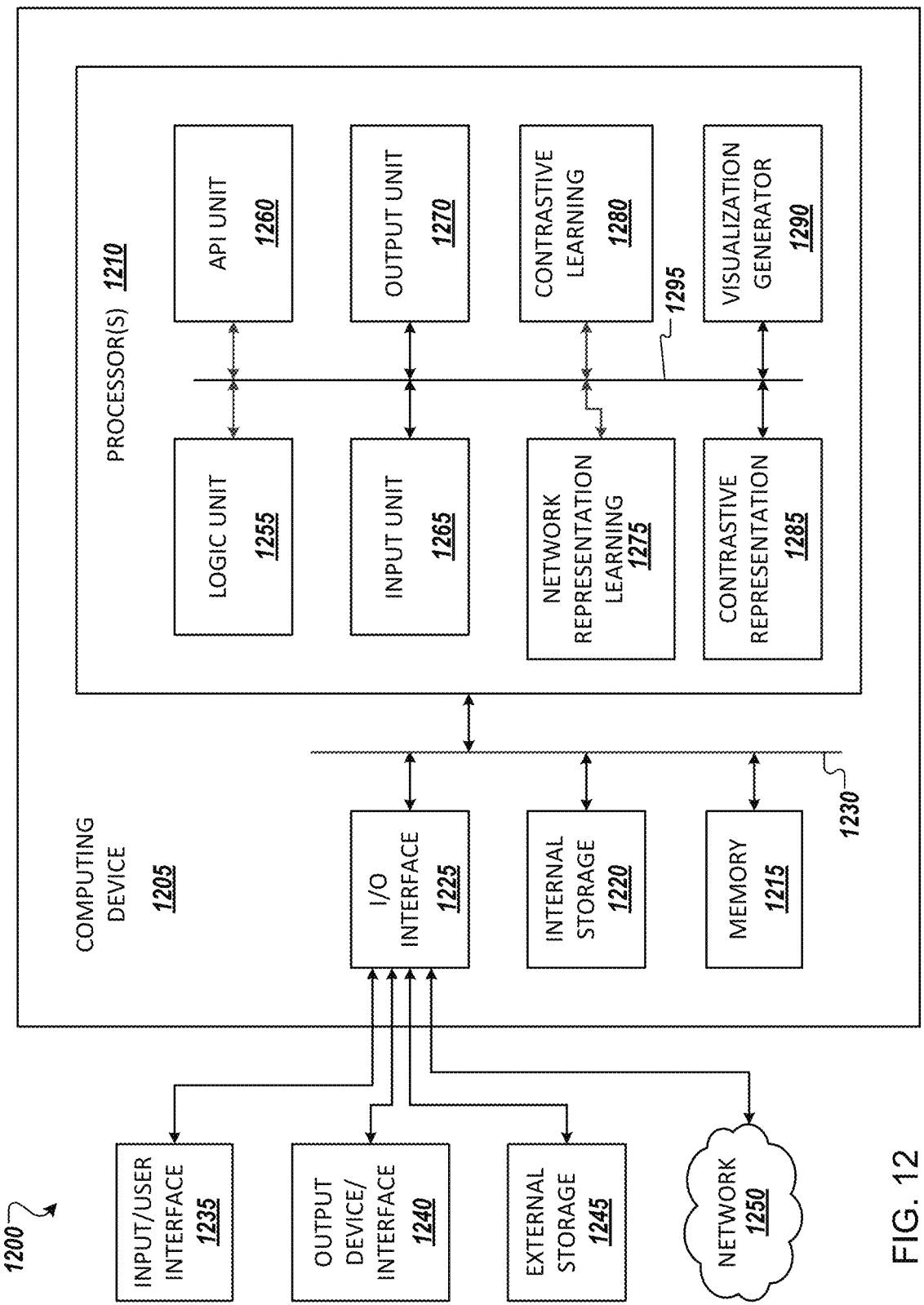
FIG. 12 illustrates an example computing environment with an example computer device suitable for use in some example implementations.

FIG. 12 illustrates an example computing environment 1200 with an example computer device 1205 suitable for use in some example implementations. Computing device 1205 in computing environment 1200 can include one or more processing units, cores, or processors 1210, memory 1215 (e.g., RAM, ROM, and/or the like), internal storage 1220 (e.g., magnetic, optical, solid state storage, and/or organic), and/or I/O interface 1225, any of which can be coupled on a communication mechanism or bus 1230 for communicating information or embedded in the computing device 1205.

Computing device 1205 can be communicatively coupled to input/interface 1235 and output device/interface 1240. Either one or both of input/interface 1235 and output device/interface 1240 can be a wired or wireless interface and can be detachable. Input/interface 1235 may include any device, component, sensor, or interface, physical or virtual, which can be used to provide input (e.g., buttons, touch-screen interface, keyboard, a pointing/cursor control, microphone, camera, braille, motion sensor, optical reader, and/or the like).

Output device/interface 1240 may include a display, television, monitor, printer, speaker, braille, or the like. In some example implementations, input/interface 1235 (e.g., user interface) and output device/interface 1240 can be embedded with, or physically coupled to, the computing device 1205. In other example implementations, other computing devices may function as, or provide the functions of, an input/interface 1235 and output device/interface 1240 for a computing device 1205. These elements may include, but are not limited to, well-known AR hardware inputs so as to permit a user to interact with an AR environment.

Examples of computing device 1205 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, server devices, other computers, information kiosks, televisions with one or more processors embedded therein and/or coupled thereto, radios, and the like).

Computing device 1205 can be communicatively coupled (e.g., via I/O interface 1225) to external storage 1245 and network 1250 for communicating with any number of networked components, devices, and systems, including one or more computing devices of the same or different configuration. Computing device 1205 or any connected computing device can be functioning as, providing services of, or referred to as a server, client, thin server, general machine, special-purpose machine, or another label.

I/O interface 1225 can include, but is not limited to, wired and/or wireless interfaces using any communication or I/O protocols or standards (e.g., Ethernet, 802.11xs, Universal System Bus, WiMAX, modem, a cellular network protocol, and the like) for communicating information to and/or from at least all the connected components, devices, and network in computing environment 1200. Network 1250 can be any network or combination of networks (e.g., the Internet, local area network, wide area network, a telephonic network, a cellular network, satellite network, and the like).

Computing device 1205 can use and/or communicate using computer-usable or computer-readable media, including transitory media and non-transitory media. Transitory media includes transmission media (e.g., metal cables, fiber optics), signals, carrier waves, and the like. Non-transitory media includes magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computing device 1205 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C#, Java, Visual Basic, Python, Perl, JavaScript, and others).

Processor(s) 1210 can execute under any operating system (OS) (not shown), in a native or virtual environment. One or more applications can be deployed that include logic unit 1255, application programming interface (API) unit 1260, input unit 1265, output unit 1270, network representation learning unit 1275, contrastive learning unit 1280, contrastive representation unit 1285, visualization generator 1290 and inter-unit communication mechanism 1295 for the different units to communicate with each other, with the OS, and with other applications (not shown).

For example network representation learning unit 1275, contrastive learning unit 1280, contrastive representation unit 1285, and visualization generator 1290 may implement one or more processes shown in FIG. 6 and implement the architectures of FIGS. 1-3. The described units and elements can be varied in design, function, configuration, or implementation and are not limited to the descriptions provided.

In some example implementations, when information or an execution instruction is received by API unit 1260, it may be communicated to one or more other units (e.g., network representation learning unit 1275, contrastive learning unit 1280, contrastive representation unit 1285, and visualization generator 1290). For example, network representation learning unit 1275 may generate feature matrices from target and background networks and provide the generated feature matrices to the contrastive learning unit 1280. The contrastive learning unit 1280 may use the generated feature matrices to generate a projection matrix through contrastive learning and provide the projection matrix to the contrastive represent unit 1285. The contrastive representation unit 1285 may use the projection matrix to generate contrastive representations of the target network and the background network from the feature matrices. Further, the visualization generator 1290 may generate a contrastive visualization based on the contrastive representations of the target network and the background network.

In some instances, the logic unit 1255 may be configured to control the information flow among the units and direct the services provided by API unit 1260, input unit 1265, post word encoder unit 1275, overall content post encoder 1280, thread decoder 1285, and summary generator 1290 in some example implementations described above. For example, the flow of one or more processes or implementations may be controlled by logic unit 1255 alone or in conjunction with API unit 1260.

Although a few example implementations have been shown and described, these example implementations are provided to convey the subject matter described herein to people who are familiar with this field. It should be understood that the subject matter described herein may be implemented in various forms without being limited to the described example implementations. The subject matter described herein can be practiced with those specifically defined or described matters or with other or different elements or matters not described. It will be appreciated by those familiar with this field that changes may be made in these example implementations without departing from the subject matter described herein, as defined in the appended claims and their equivalents.

What is claimed is:

1. A method of analyzing a target network relative to a background network of data using machine learning, the method comprising:
    extracting a first feature matrix from an adjacency matrix representative of the target network;
    extracting a second feature matrix from an adjacency matrix representative of the background network;
    generating a projection matrix based on the first and second feature matrices using a contrastive learning algorithm;
    generating a first contrastive matrix representation of the target network based on the projection matrix and the first feature matrix;
    generating a second contrastive matrix representation of the background network based on the projection matrix and the second feature matrix; and
    displaying a visualization of unique features of the target network relative to the background network based on the first contrastive matrix and the second contrastive matrix.

2. The method of claim 1, wherein the first feature matrix is extracted from the adjacency matrix representative of the target network using a network learning algorithm; and
    wherein the second feature matrix is extracted from the adjacency matrix representative of the target network using the network learning algorithm.

3. The method of claim 2, wherein the network learning algorithm is a DeepGL algorithm.

4. The method of claim 1, wherein the target network is a neuron network representation associated with a patient generated at a specific time;
    wherein the background network is a neuron network representation associated with the patient generated at a prior time before the specific time; and
    wherein the method further comprises identifying changes in the neuron network representation associated with the patient generated at a specific time based on the visualized unique features of the target network.

5. The method of claim 1, wherein the target network is a social collaboration network associated with a research domain generated at a specific time;
    wherein the background network is a social collaboration network associated with a research domain generated at a prior time before the specific time; and
    wherein the method further comprises identifying changes in the social collaboration network associated with a research domain generated at a specific time based on the visualized unique features of the target network.

6. The method of claim 1, wherein the target network is a network representation of phenotypic features of a first biological species;
    wherein the background network is a network representation of phenotypic features of a second, related biological species; and
    wherein the method further comprises identifying distinctive phenotypic features of the first biological species based on the visualized unique features of the target network.

7. The method of claim 1, wherein the target network is a network representation of links between symptoms found in patients diagnosed with a first biological disease;
    wherein the background network is a network representation of links between symptoms found in patients diagnosed with a second biological disease; and
    wherein the method further comprises identifying distinctive symptoms unique to the first biological disease based on the visualized unique features of the target network.

8. The method of claim 1, wherein the target network is a real world network being modeled by a network modeling application;
    wherein the background network is a model network representative of the real world network generated by the network modeling application; and
    wherein the method further comprises updating the network modeling application to include the visualized unique features of the target network.

9. A non-transitory computer readable medium encoded with instructions for making a computing device execute a method of analyzing a target network relative to a background network of data using machine learning, the method comprising:
    extracting a first feature matrix from an adjacency matrix representative of the target network;
    extracting a second feature matrix from an adjacency matrix representative of the background network;
    generating a projection matrix based on the first and second feature matrices using a contrastive learning algorithm;
    generating a first contrastive matrix representation of the target network based on the projection matrix and the first feature matrix;
    generating a second contrastive matrix representation of the background network based on the projection matrix and the second feature matrix; and
    displaying a visualization of unique features of the target network relative to the background network based on the first contrastive matrix and the second contrastive matrix.

10. The non-transitory computer readable medium of claim 9, wherein the first feature matrix is extracted from the adjacency matrix representative of the target network using a network learning algorithm;

wherein the second feature matrix is extracted from the adjacency matrix representative of the target network using the network learning algorithm; and wherein the network learning algorithm is a DeepGL algorithm.

11. The non-transitory computer readable medium of claim 9, wherein the target network is a neuron network representation associated with a patient generated at a specific time;

wherein the background network is a neuron network representation associated with the patient generated at a prior time before the specific time; and wherein the method further comprises identifying changes in the neuron network representation associated with the patient generated at a specific time based on the visualized unique features of the target network.

12. The non-transitory computer readable medium of claim 9, wherein the target network is a social collaboration network associated with a research domain generated at a specific time;

wherein the background network is a social collaboration network associated with a research domain generated at a prior time before the specific time; and wherein the method further comprises identifying changes in the social collaboration network associated with a research domain generated at a specific time based on the visualized unique features of the target network.

13. The non-transitory computer readable medium of claim 9, wherein the target network is a network representation of phenotypic features of a first biological species;

wherein the background network is a network representation of phenotypic features of a second, related biological species; and wherein the method further comprises identifying distinctive phenotypic features of the first biological species based on the visualized unique features of the target network.

14. The non-transitory computer readable medium of claim 9, wherein the target network is a network representation of links between symptoms found in patients diagnosed with a first biological disease;

wherein the background network is a network representation of links between symptoms found in patients diagnosed with a second biological disease; and wherein the method further comprises identifying distinctive symptoms unique to the first biological disease based on the visualized unique features of the target network.

15. The non-transitory computer readable medium of claim 9, wherein the target network is a real world network being modeled by a network modeling application;

wherein the background network is a model network representative of the real world network generated by the network modeling application; and wherein the method further comprises updating the network modeling application to include the visualized unique features of the target network.

16. A computing device comprising:

a storage device storing network data associated with a target network and a background network; and a processor encoded to execute a method of automatically analyzing the target network relative to the background network of data using machine learning, the method comprising:

extracting a first feature matrix from an adjacency matrix representative of the target network;

extracting a second feature matrix from an adjacency matrix representative of the background network;

generating a projection matrix based on the first and second feature matrices using a contrastive learning algorithm;

generating a first contrastive matrix representation of the target network based on the projection matrix and the first feature matrix;

generating a second contrastive matrix representation of the background network based on the projection matrix and the second feature matrix; and displaying a visualization of unique features of the target network relative to the background network based on the first contrastive matrix and the second contrastive matrix.

17. The computing device of claim 16, wherein the target network is a neuron network representation associated with a patient generated at a specific time;

wherein the background network is a neuron network representation associated with the patient generated at a prior time before the specific time; and wherein the method further comprises identifying changes in the neuron network representation associated with the patient generated at a specific time based on the visualized unique features of the target network.

18. The computing device of claim 16, wherein the target network is a social collaboration network associated with a research domain generated at a specific time;

wherein the background network is a social collaboration network associated with a research domain generated at a prior time before the specific time; and wherein the method further comprises identifying changes in the social collaboration network associated with a research domain generated at a specific time based on the visualized unique features of the target network.

19. The computing device of claim 16, wherein the target network is a network representation of phenotypic features of a first biological species;

wherein the background network is a network representation of phenotypic features of a second, related biological species; and wherein the method further comprises identifying distinctive phenotypic features of the first biological species based on the visualized unique features of the target network.

20. The computing device of claim 16, wherein the target network is a network representation of links between symptoms found in patients diagnosed with a first biological disease;

wherein the background network is a network representation of links between symptoms found in patients diagnosed with a second biological disease; and wherein the method further comprises identifying distinctive symptoms unique to the first biological disease based on the visualized unique features of the target network.

21. The computing device of claim 16, wherein the target network is a real world network being modeled by a network modeling application;

wherein the background network is a model network representative of the real world network generated by the network modeling application; and wherein the method further comprises updating the network modeling application to include the visualized unique features of the target network.

* * * * *